United States Patent [19]

Casey et al.

[11] 4,429,080

[45] Jan. 31, 1984

[54] SYNTHETIC COPOLYMER SURGICAL ARTICLES AND METHOD OF MANUFACTURING THE SAME

[75] Inventors: Donald J. Casey, Ridgefield; Mark S. Roby, Stamford, both of Conn.

[73] Assignee: American Cyanamid Company, Stamford, Conn.

[21] Appl. No.: 394,347

[22] Filed: Jul. 1, 1982

[51] Int. Cl.³ .................... C08G 63/76; C08L 67/00
[52] U.S. Cl. .................... 525/415; 128/346; 128/334 R., 528/354
[58] Field of Search .................... 525/415; 528/354; 128/333.5, 346

[56] References Cited

U.S. PATENT DOCUMENTS

| | | | |
|---|---|---|---|
| 4,080,969 | 3/1978 | Casey et al. | 528/354 X |
| 4,137,921 | 2/1979 | Okuzumi et al. | 528/354 X |
| 4,157,437 | 6/1979 | Okuzumi et al. | 528/354 |
| 4,190,720 | 2/1980 | Shalaby | 528/354 |
| 4,243,775 | 1/1981 | Rosensaft et al. | 525/415 |
| 4,300,565 | 11/1981 | Rosensaft et al. | 525/415 X |

FOREIGN PATENT DOCUMENTS 2849785  5/1979  Fed. Rep. of Germany ...... 525/415

*Primary Examiner*—Lucille M. Phynes
*Attorney, Agent, or Firm*—Charles F. Costello, Jr.; Alphonse R. Noe

[57] ABSTRACT

A triblock copolymer having a proportion of units having the formula:

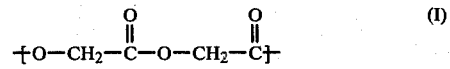

as the end blocks, and the formula (I) randomly combined with a proportion of units having the formula:

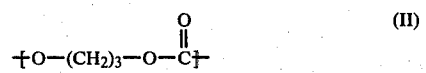

as the middle block finds particular advantageous use in manufacturing absorbable monofilament sutures and other surgical articles. A surgical article is manufactured from a synthetic absorbable copolymer formed by copolymerizing glycolide with 1,3-dioxan-2-one (trimethylene carbonate) wherein a combination of the monomers is substantially completely polymerized before the addition of the other monomer in the presence of a difunctional initiator at or below about 180° C.; glycolide is added and the temperature increased up to about the melting point of poly glycolide to form a triblock copolymer with a proportion of units having the formula:

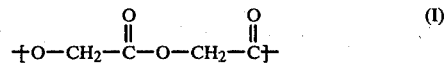

as the end blocks, and the formula (I) randomly combined with a proportion of units having the formula:

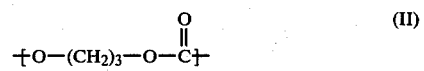

as the middle block.

10 Claims, No Drawings

SYNTHETIC COPOLYMER SURGICAL ARTICLES AND METHOD OF MANUFACTURING THE SAME

BACKGROUND OF THE INVENTION

This invention relates to a copolymer, and more particularly to a surgical article manufactured from the copolymer and to a method of manufacturing and using the surgical article.

Absorbable synthetic polymer sutures known in the prior art are usually manufactured, sold, and used as braids. The known absorbable polymers containing a glycolic acid ester linkage seem to be well suited for use as such braided sutures. However, some of them tend to form relatively stiff monofilaments, particularly in the larger diameters. Yet, some surgeons prefer the suturing characteristics of a smooth, continuous-surfaced monofilament suture. Thus, it has been recognized for some years that there is a need in surgery for flexible, absorbable, monofilament sutures which retain a safe and useful proportion of their strength for a relatively long period of time in vivo.

To be fully useful as an absorbable suture it is essential that a monofilament not only be absorbable and flexible but it must also be capable of a relatively long period of in vivo strength retention. An appropriate strength retention target for this type monofilament suture is considered to be about 35–42 days in vivo.

U.S. Pat. No. 4,243,775, Rosensaft and Webb, assigned to the assignee of the present invention, discloses a polymer material useful for forming both an absorbable braided suture and, under certain conditions, a flexible monofilament suture with extended strength retention. That patent discloses the sequential addition of a cyclic ester monomer, such as a lactide, lactone, oxalate or carbonate, to glycolide monomer in the copolymerization process using a monofunctional alcohol as an initiator. Disclosed are triblock copolymers with poly(lactide) units predominantly on both ends of a glycolide polymer chain, copolymers of trimethylene carbonate (1,3-dioxan-2-one) and glycolide, and monofilament sutures made therefrom.

In the glycolide-trimethylene carbonate copolymer monofilament of U.S. Pat. No. 4,243,775, flexibility and extended strength retention are obtained at high incorporation of the 1,3-dioxan-2-one. The disclosed triblock copolymer comprises poly(lactide) units as the end blocks and poly(glycolide) units as the middle block and is formed using a monofunctional alcohol.

The present invention provides a glycolide-trimethylene carbonate triblock copolymer that results in a monofilament suture which has an increased absorption rate compared to the glycolide-trimethylene carbonate copolymer suture of U.S. Pat. No. 4,243,775. The present invention also provides a method of producing the desired copolymer which is easier to carry out than the polymerization process disclosed in that patent.

SUMMARY OF THE INVENTION

The foregoing is achieved, according to the present invention, by designing a particular polymer construction and selecting a particular composition to produce a monofilament suture of a triblock copolymer possessing improved flexibility and extended strength retention compared to known absorbable sutures while retaining an acceptable absorption rate. It has been discovered that, surprisingly, the advantages discussed are obtained by the provision of a triblock copolymer comprising a proportion of units having the formula:

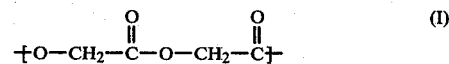

as the end blocks, and the formula (I) randomly combined with a proportion of units having the formula:

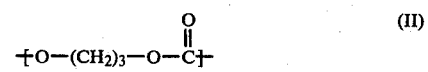

as the middle block.

The invention further comprises an improvement in the method for the manufacture of a surgical article manufactured from a synthetic absorbable copolymer formed by copolymerizing glycolide with 1,3-dioxan-2-one, wherein a combination of the monomers is substantially completely polymerized before the addition of the other monomer, the improvement comprising substantially completely polymerizing the combination at or below 180° C. in the presence of a difunctional initiator; adding glycolide; and increasing the temperature up to about the melting point of polyglycolide to form a triblock copolymer comprising a proportion of units having the formula:

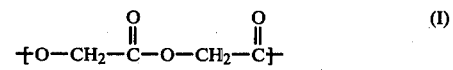

as the end blocks, and the formula (I) randomly combined with a proportion of units having the formula:

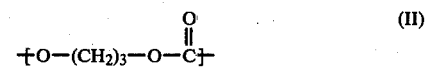

as the middle block.

Unexpectly good results as an absorbable, flexible monofilament surgical suture of extended strength retention are obtained when the weight ratio of units of formula (I) to those of formula (II) approaches 67.5:32.5 overall and 15:85 in the middle block.

The invention has several advantages. One advantage is ease of manufacture. In the process used for preparing the random triblock copolymers of this invention, a difunctional initiator, glycol, is employed as an initiator and the glycolide-trimethylene carbonate middle block is synthesized first at around 180° C. The temperature is then raised to around 220° C. to prevent crystallization of the copolymer as it forms and glycolide is added to form the polyglycolide end blocks. If a monofunctional alcohol were used in the monomers of the present invention, it would be necessary to form one poly(glycolide) end block, then add trimethylene carbonate and more glycolide to form the middle block, and when this mixture is substantially completely polymerized, to make a third addition of glycolide to form the final poly(glycolide) end block. The high polyglycolide melting point would require that each of these steps be carried out at around 220° C.

The present invention provides an operationally simpler approach to producing triblock polyesters. Only two monomer additions are required rather than three as in the prior art; thus reducing the possibility for operator charging errors, the possibility for adventitious contamination of the polymerization during charging, and the possibility that successive blocks will differ from the desired composition as a result of unreacted monomer from a preceding block. The lower temperature used for part of the polymerization cycle may permit formation of somewhat higher molecular weight copolymer, in contrast to the prior art, expected to afford improved fiber quality. The shorter reaction time at around 220° C. should reduce the extent of transesterification or scrambling among the three blocks and thereby produce a sequence of monomer units closer to the desired arrangement of poly(glycolide)-poly(glycolide-co-trimethylene carbonate)-poly(glycolide). Also, the lower reaction temperatures used in the step involving the less thermally stable trimethylene carbonate monomer aids in reducing thermal degradation of this monomer.

A further advantage is that the triblock copolymer is formed by only one sequential addition of monomer to the middle block prepolymer formed using a difunctional initiator and a combination of monomers.

Thus, an object of this invention is the provision of a triblock copolymer of glycolide-trimethylene carbonate for producing absorbable surgical articles such as sutures.

A further object of this invention is the provision of a method of polymerization for producing a triblock copolymer of glycolide-trimethylene carbonate which is easier to control and carry out.

The difunctional initiator is advantageously selected from the group consisting of a glycol or polyol; wherein the initiator is a glycol; and wherein the glycol is diethylene glycol. The polymerization advantageously occurs at a temperature of about 160° to 190° C.; and most advantageously at about 180° C.

The middle block is advantageously about 20-60% by weight, of the total copolymer.

The copolymers of the invention find advantageous utility in the manufacture of surgical articles and pharmaceutical compositions as is known in the art for polymer absorbable in living animals. Thus, yet further objects of this invention include the provision of a sterile surgical article, a suture or ligature, a suture in the form of a needle and a suture combination, a surgical clip or staple, a surgical prosthesis, textile structures, couplings, tubes or other forms of support or a self-supporting film, hollow tube, beads or gel, containing a uniformly dispersed drug for controlled continuous administration, manufactured from a copolymer or by a method described above. Yet other objects of this invention include the provision of a method of retaining living tisue in a desired relationship during a healing process by positioning and emplacing living tissue with a surgical article or a suture or ligature or a staple or a support described above and a method of closing a wound of living tissue comprising sewing the edges of the wound with a needled suture described above and a method for continuous controlled release administration of a predetermined dosage of a pharmaceutical composition.

The foregoing and other objects, features and advantages of this invention will be further apparent from the following description of preferred embodiments thereof and from the claims appended hereto.

DESCRIPTION OF THE PREFERRED EMBODIMENTS

The polyesters of this invention are triblock copolymers. The two end blocks are comprised of a proportion of sequential units having the formula:

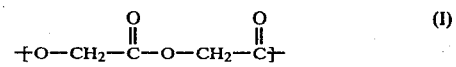

The middle block is comprised of a copolymer comprising a proportion of random units having the formula (I) and:

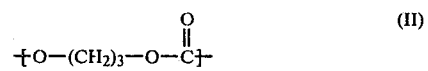

The procedure used to form the middle block involves mixing the glycolide and 1,3-dioxan-2-one monomers in a reactor in the presence of a difunctional initiator to form what is commonly termed a random copolymer. The structure of the middle block is determined by the reactivity ratios of the two monomers and may consist of a random sequence of monomer units or a more regular distribution of the respective monomers.

In the process used for preparing the triblocks of this invention, a glycol is employed as an initiator and $SnCl_2.2H_2O$ as a catalyst and the middle block comprising a proportion of units having the formula:

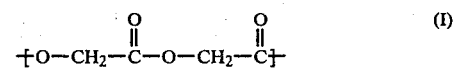

randomly combined with a proportion of units having the formula:

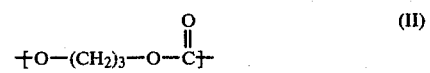

is synthesized first at or below about 180° C. The temperature is then raised to 220° C. to prevent crystallization of the copolymer as it forms. As the temperature is raised, glycolide is added to form the end blocks composed of sequential units of formula (I).

The structure of the middle block can be controlled by feeding the two monomers to the reactor in proportion to their reactivity ratios. In the present invention both middle block monomers are charged together to form a middle block in which units of formula (I) are randomly dispersed in units of formula (II).

It is generally preferred to conduct the consecutive polymerizations in the same reaction vessel by sequentially adding the monomers. However, if desired, one of the polymer segments can be prepared and used as a pre-formed segment for further chemical reaction to form the final copolymer in a different reaction vessel.

A catalyst other than $SnCl_2.2H_2O$ can be used in the method of this invention. Also, an initiator other than a glycol and specifically other than diethylene glycol can be used. Other catalysts and initiators can be, e.g.:

| Catalysts | Initiators |
| --- | --- |
| Stannous chloride | 1,4-butanediol |
| Dibutyl tin dilaurate | 1,5-pentanediol |

| Catalysts | Initiators |
|---|---|
| Dibutyl tin diacetate | 1,6-hexanediol |
| Dibutyl tin dichloride | 1,10-decanediol |
| Stannic chloride pentahydrate | inositol |
| Aluminum isopropoxide | pentaerythritol |
| Antimony trioxide | mannitol |
| Stannous fluoride | sorbitol |
| Stannous citrate | erythritol |
| Stannous acetate | ethylene glycol |
| Antimony trifluoride | 1,3-propane diol |
| Tin teteraisopropoxide | |
| Lead oxide | |
| Tetra isopropyl titanate | |
| Titanium acetyl acetonate | |
| Tetraoctylene glycol titanate | |
| Boron Trifluoride etherate | |
| Aluminum Trichloride | |

The preferred area for use of the present invention is in the preparation of sterile synthetic absorbable surgical articles, specifically sutures, wherein glycolide is employed as the predominant monomer. Absorbable monofilament sutures fabricated from such copolymers have been found to be useful in that they are more flexible and more resistant to in vivo strength loss than large size monofilament sutures fabricated from a state-of-the-art polymer containing a glycolic acid ester linkage.

The surgical articles are fabricated from the copolymer using conventionally employed procedures and subsequently sterilized. The resulting surgical articles are employed in a conventional manner.

The following examples illustrate procedures which are useful in conjunction with the practice of the present invention but are not to be taken as being limiting thereto.

EXAMPLE 1

Trimethylene carbonate (80 g) and glycolide (14 g) were melted together in a dry flask. Diethylene glycol (0.043 ml) containing $SnCl_2.2H_2O$ (0.9714 g/10 ml) was then added to the melt and the flask contents were charged to a stirred reactor which had been preheated to 162° C. under a stream of nitrogen. After 75 minutes, the temperature was increased to 183° C. over a period of 20 minutes. A sample (6 g) of this middle block was removed and glycolide (12 g) was added. Over the next 15 minutes, the temperature was raised to 197° C. at which time more glycolide (104 g) was added. The temperature was increased to 220° C. over a period of 15 minutes. The reaction mixture was stirred at 220° C. for 10 minutes and then the copolymer was discharged. The solidified polymer was ground in a Wiley Mill to pass through a 10 mesh screen and then dried at 130° C. (1 mm Hg) for 48 hours.

The 6 g middle block sample removed at 183° C. had an inherent viscosity, (the inherent viscosity was measured here and hereinafter using a solution of 0.5 grams of copolymer per 100 milliliters of hexafluoroacetone sesquihydrate (HFAS) at 30 degrees C.), of 1.39 and consisted of 86 mole percent or 84 weight percent of trimethylene carbonate units as determined by NMR analysis.

The final copolymer had an inherent viscosity of 1.19 and contained 36 mole percent or 33 weight percent of trimethylene carbonate. Differential scanning calorimetry indicated the final copolymer had a glass transition temperature of 19° C., a peak melting endotherm of 202° C. and a heat of fusion of 30 J/g.

EXAMPLE 2

A fiber was formed from the copolymer of Example 1 by melting the copolymer at 225° C. and pumping the melt through a 50 mil capillary possessing a 4/1 length to diameter ratio. The extrudate was quenched by passage through a water bath and collected on a bobbin at a rate of 10 feet per minute.

The fiber was then drawn through a two zone air chamber. In the first zone the fiber was drawn 7.1× at 40° C. and in the second zone the fiber was drawn 1.3× at 45° C. The fiber was then post-treated by heating at 100° C. (1 mm Hg) for 3 hours.

The physical properties of the drawn and post-treated fiber were:
Straight Pull Tensile Strength: 43,000 psi
Straight Pull Elongation at Break: 23%
Knot Pull Strength: 56,000 psi
Modulus: 137,000 psi
Diameter: 0.251 mm

EXAMPLE 3

Trimethylene carbonate (78 g) and glycolide (3 g) were melted together in a dry flask. Diethylene glycol (0.018 ml) containing $SnCl_2.2H_2O$ (0.0971 g/ml) was then added to the melt and the flask contents were charged to a stirred reactor which had been preheated to 158° C. under a stream of nitrogen. After 60 minutes, the temperature was raised to 183° C. over a period of 30 minutes. This temperature was maintained for 30 minutes at which time, a sample (5 g) of the middle block was removed. Ether (3.0 ml) containing $SnCl_2.2H_2O$ ($8.10 \times 10^{-4}$ g/ml) was added to a flask containing glycolide (122 g). After removing the ether under vacuum, approximately 12 g of the glycolide was added to the reactor. The temperature was increased to 195° C. over 9 minutes at which time the remaining glycolide was added. Over the next 10 minutes, the temperature was raised to 219° C. The reaction mixture was stirred at 219° C. for 5 minutes, and then the copolymer was discharged. The solidified polymer was ground in a Wiley Mill to pass through a 10 mesh screen and was dried at 130° C. (1 mm Hg) for 48 hours.

The 5 g middle block sample removed at 183° C. had an inherent viscosity of 1.25 and consisted of 95.6 mole percent or 95.0 weight percent trimethylene carbonate units as determined by NMR analysis.

The final copolymer had an inherent viscosity of 1.20 and contained 39.0 mole percent or 36.0 weight percent trimethylene carbonate. Differential scanning calorimetry indicated a glass transition temperature of 27° C., a peak melting endotherm of 214° C. and a heat of fusion of 44 J/g were determined.

EXAMPLE 4

Trimethylene carbonate (78 g) and glycolide (8.5 g) were melted together in a dry flask. Diethylene glycol (0.038 ml) containing $SnCl_2.2H_2O$ (0.0971 g/ml) was then added to the melt and the flask contents were charged to a stirred reactor which had been preheated to 159° C. under a stream of nitrogen. After 37 minutes, the temperature was raised to 180° C. over a period of 20 minutes. This temperature was maintained for 40 minutes at which time, a sample (5 g) of the middle block was removed and glycolide (12 g) was added. The temperature was increased to 212° C. over 9 minutes at which time additional glycolide (106 g) was added. Over the next 12 minutes, the temperature was raised to 219° C. The reaction mixture was stirred at 219° C. for 11 minutes and then the copolymer was discharged. The solidified polymer was ground in a Wiley Mill to pass through a 10 mesh screen and was dried at 130° C. (1 mm Hg) for 48 hours.

The 5 g middle block sample removed at 180° C. had an inherent viscosity of 1.31 and consisted of 91.5 mole percent or 90.4 weight percent trimethylene carbonate units as determined by NMR analysis.

The final copolymer had an inherent viscosity of 1.06 and contained 46.5 mole percent or 43.3 weight percent trimethylene carbonate. Differential scanning calorimetry indicated a glass transition temperature of 27° C., a peak melting endotherm of 213° C. and a heat of fusion of 41 J/g were determined.

EXAMPLE 5

Trimethylene carbonate (70 g) and glycolide (30 g) were melted together in a dry flask. Diethylene glycol (0.043 ml) containing $SnCl_2.2H_2O$ (0.0971 g/ml) was then added to the melt and the flask contents were charged to a stirred reactor which had been preheated to 160° C. under a stream of nitrogen. After 22 minutes, the temperature was raised to 180° C. over a period of 25 minutes. This temperature was maintained for 69 minutes at which time, a sample (5 g) of the middle block was removed and glycolide (11 g) was added. The temperature was increased to 205° C. over 14 minutes at which time additional glycolide (103 g) was added. Over the next 13 minutes, the temperature was raised to 220° C. The reaction mixture was stirred at 220° C. for 12 minutes at this temperature and then the copolymer was discharged. The solidified polymer was ground in a Wiley Mill in order to pass through a 10 mesh screen and was dried at 130° C. (1 mm Hg) for 48 hours.

The 5 g middle block sample removed at 180° C. had an inherent viscosity of 1.34 and consisted of 73.0 mole percent of 70.4 weight percent trimethylene carbonate units as determined by NMR analysis.

The final copolymer had an inherent viscosity of 1.06 and contained 46.5 mole percent or 43.3 weight percent trimethylene carbonate. Differential scanning calorimetry indicated a glass transition temperature of 27° C., a peak melting endotherm of 213° C. and a heat of fusion of 41 J/g were determined.

EXAMPLE 5

Trimethylene carbonate (70 g) and glycolide (30 g) were melted together in a dry flask. Diethylene glycol (0.043 ml) containing $SnCl_2.2H_2O$ (0.0971 g/ml) was then added to the melt and the flask contents were charged to a stirred reactor which had been preheated to 160° C. under a stream of nitrogen. After 22 minutes, the temperature was raised to 180° C. over a period of 25 minutes. This temperature was maintained for 69 minutes at which time, a sample (5 g) of the middle block was removed and glycolide (11 g) was added. The temperature was increased to 205° C. over 14 minutes at which time additional glycolide (103 g) was added. Over the next 13 minutes, the temperature was raised to 220° C. The reaction mixutre was stirred at 220° C. for 12 minutes at this temperature and then the copolymer was discharged. The solidified polymer was ground in a Wiley Mill in order to pass through a 10 mesh screen and was dried at 130° C. (1 mm Hg) for 48 hours.

The 5 g middle block sample removed at 180° C. had an inherent viscosity of 1.34 and consisted of 73.0 mole percent of 70.4 weight percent trimethylene carbonate units as determined by NMR analysis.

The final copolymer had an inherent viscosity of 1.23 and contained 33.1 mole percent of 30.3 weight percent trimethylene carbonate.

EXAMPLE 6

Trimethylene carbonate (78 g) and glycolide (19.5 g) were melted together in a dry flask. Diethylene glycol (0.24 ml) containing $SnCl_2.2H_2O$ (0.0971 g/ml) was added to the melt and the flask contents were charged to a stirred reactor which had been preheated to 160° C. under a stream of nitrogen. After 68 minutes, the temperature was raised to 179° C. over a period of 19 minutes. This temperature was maintained for 30 minutes at which time, a sample (5 g) of the middle block was removed. Ether (3.1 ml) containing $SnCl_2.2H_2O$ ($6.98 \times 10^{-4}$ g/ml) was added to a flask containing glycolide (107.5 g). After removing the ether under vacuum, approximately 8 g of the glycolide was added to the reactor. The temperature was increased to 189° C. over 12 minutes at which time the remaining glycolide was added. Over the next 16 minutes the temperature was raised to 221° C. The copolymer was discharged, cooled and ground in a Wiley Mill in order to pass through a 10 mesh screen. The polymer was then dried at 130° C. (1 mm Hg) for 48 hours.

The 5 g middle block sample removed at 179° C. had an inherent viscosity of 1.01 and consisted of 82.0 mole percent or 81.0 weight percent trimethylene carbonate units as determined by NMR analysis.

The final copolymer had an inherent viscosity of 0.92 and contained 33.8 mole percent or 36.7 weight percent trimethylene carbonate. Differential scanning calorimetry indicated a glass transition temperature of 17° C., a peak melting endotherm of 190° C. and a heat of fusion of 20 J/g were determined.

EXAMPLES 7-10

The copolymers described in examples 3-6 were extruded into monofilament fibers in a fashion similar to that used in Example 2. Samples of the monofilaments were implanted subcutaneously in rats, removed after 21, 35, 42 and 49 days and their straight pull tensil strength measured to determine the percentage of original strength retained in vivo. Samples of the monofilaments were also implanted in rabbits and observed after 180 and 270 days to determine the percentage of polymer absorbed in vivo.

The procedure for determining in vivo strength retention involves implanting sutures subcutaneously at right angles to the central abdominal midline in groups of rats corresponding to the number of intervals to be observed. The rats of a group are sacrificed after the time period involved and the sutures retrieved from the implant sites. Breaking strength is measured using an Instron tensiometer. For each suture implanted, the percentage of initial breaking strength retained was calculated by dividing the breaking strength by the mean of the initial strength for that suture.

The in vivo absorption percentage is determined by implanting suture segments in anterior and posterior implantation sites in rabbits, sacrificing the animals at the end of the time period to be observed and removing en bloc histological sections of the implant site. The percentage of the suture segment remaining, that is, not yet absorbed, is determined. From this the amount absorbed is calculated. Fiber and in vivo properties are summarized in Tables 1 and 2 for Examples 7-10.

TABLE 1

| | Fiber Properties For Examples 7-10 | | | | | |
|---|---|---|---|---|---|---|
| | Wt % PTMC | | Straight Pull (psi) | Knot Pull (psi) | % E | Bending Modulus (psi) |
| Example | Middle Block | Final Copolymer | | | | |
| 7 | 95.0 | 36.3 | 50,000 | 53,000 | 18 | 481,000 |
| 8 | 90.4 | 42.6 | 40,000 | 40,000 | 28 | 370,000 |
| 9 | 70.4 | 30.3 | 60,000 | 47,000 | 21 | 137,000 |
| 10 | 80.5 | 33.8 | 47,000 | 42,000 | 24 | 56,000 |

TABLE 2

| | In Vivo Strength Retention (%) | | | | In Vivo Absorption (%) | |
|---|---|---|---|---|---|---|
| Example | 21 | 35 | 42 | 49 | 180 | 270 |
| 7 | 70 | 29 | 19 | 8 | 84 | — |
| 8 | 67 | 42 | 28 | 18 | 12 | — |
| 9 | 47 | 15 | 6 | 0 | 59 | — |
| 10 | 61 | 27 | 18 | 6 | 93 | 100 |

The results of Examples 7-10 demonstrate that the sutures made from triblock copolymers according to this invention retain on average, over 60 percent of their strength, in vivo, after 21 days. Moreover, as the compositions approach approximately 35 percent trimethylene carbonate polymer in the overall copolymer and 85 percent in the middle block, absorption is very good. This is borne out further by the results of similar evaluation on other percentage compositions of the triblock copolymer, Examples 11-15, set forth in Table 3.

TABLE 3

| | Wt % PTMC | | Strength Pull (psi) | Bending Modulus (psi) | In Vivo Strength Retention % | | | | In Vivo Absorption % | |
|---|---|---|---|---|---|---|---|---|---|---|
| Example | Middle Block | Final Copolymer | | | 21 | 35 | 42 | 49 | 180 | 270 |
| 11 | 86 | 32 | 34,000 | 173,000 | 49 | 3 | 1 | — | 100 | 100 |
| 12 | 84 | 33 | 43,000 | 137,000 | 63 | 23 | 10 | 2 | 100 | 100 |
| 13 | 88 | 35 | 61,000 | 260,000 | 69 | 53 | 33 | 18 | 82 | 100 |
| 14 | 87 | 23 | 78,000 | 1,190,000 | 51 | 8 | 1 | 0 | 94 | 100 |
| 15 | 77 | 27 | 67,000 | 150,000 | 59 | 22 | 11 | 1 | 100 | 100 |

We claim:

1. A surgical article manufactured from a fiber having a bending modulus of less than 500,000 psi, said fiber manufactured from a triblock copolymer comprising a proportion of units having the formula:

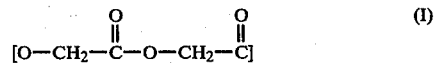
(I)

as the end blocks, said formula (I) as an end block having a hydrogen atom attached to the terminal oxygen atom, and the formula (I) randomly combined with a proportion of units having the formula:

(II)

as the middle block wherein the middle block comprises 70-95 percent, by weight, of units of formula II and the total copolymer comprises 30-40 percent, by weight, of units of formula II.

2. A method for the manufacture of a surgical article manufactured from a synthetic absorbable copolymer formed by copolymerizing glycolide with 1,3-dioxan-2-one wherein a combination of the monomers is substantially completely polymerized before the addition of the other monomer, the improvement comprising substantially completely polymerizing the combination in the presence of a difunctional initiator at about 180° C.; increasing the temperature up to about the melting point of polyglycolide; and adding glycolide to form a triblock copolymer comprising a proportion of units having the formula:

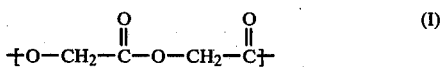
(I)

as the end blocks, and the formula (I) randomly combined with a proportion of units having the formula:

(II)

as the middle block.

3. A method of claim 2 wherein the initiator is selected from the group consisting of a glycol or a polyol.

4. A method of claim 3 wherein the initiator is a glycol.

5. A method of claim 4 wherein said glycol is diethylene glycol.

6. A method of claim 2 or 4 wherein the polymerizing of said combination is at a temperature of about 160° C. to 190° C.

7. A method of claim 6 wherein said temperature is about 180° C.

8. A method of claim 2 or 7 wherein said middle block is about 20-60 percent by weight.

9. A method of claim 8 wherein the middle block comprises 70-95 percent, by weight, of units of formula II and the total copolymer comprises 30-40 percent, by weight, of units of formula II.

10. A surgical article manufactured from copolymer made according to a method of claim 2 or 9.

* * * * *